(12) United States Patent
McBrady et al.

(10) Patent No.: US 8,196,449 B2
(45) Date of Patent: Jun. 12, 2012

(54) MICRO DISCHARGE DEVICE CAPABLE OF LOW VOLTAGE DISCHARGES IN A VARIETY OF CARRIER GASES FOR DETECTION AND/OR IONIZATION

(75) Inventors: Adam Dewey McBrady, Minneapolis, MN (US); Fouad Nusseibeh, Champlin, MN (US); Terry M. Marta, White Bear Lake, MN (US); Robert Higashi, Shorewood, MN (US)

(73) Assignee: Honeywell International Inc., Morristown, NJ (US)

( * ) Notice: Subject to any disclaimer, the term of this patent is extended or adjusted under 35 U.S.C. 154(b) by 834 days.

(21) Appl. No.: 12/262,020

(22) Filed: Oct. 30, 2008

(65) Prior Publication Data

US 2010/0045159 A1    Feb. 25, 2010

Related U.S. Application Data

(60) Provisional application No. 60/990,559, filed on Nov. 27, 2007.

(51) Int. Cl.
    *G01N 30/62*    (2006.01)
(52) U.S. Cl. .................................... 73/23.4; 73/31.05
(58) Field of Classification Search .................. 73/23.4, 73/61.58, 23.35, 25.05, 31.05; 250/281; 313/356
    See application file for complete search history.

(56) References Cited

U.S. PATENT DOCUMENTS

| | | | | |
|---|---|---|---|---|
| 3,417,606 A | * | 12/1968 | Werner et al. | 73/24.01 |
| 3,656,339 A | * | 4/1972 | Narain | 73/31.03 |
| 5,591,896 A | * | 1/1997 | Lin | 73/31.05 |
| 5,955,886 A | * | 9/1999 | Cohen et al. | 324/464 |
| 6,457,347 B1 | * | 10/2002 | Koo et al. | 73/23.35 |
| 6,736,000 B2 | * | 5/2004 | Koo et al. | 73/23.4 |
| 7,100,421 B1 | * | 9/2006 | Herring | 73/23.35 |
| 7,401,497 B2 | * | 7/2008 | Bonne et al. | 73/23.35 |
| 7,530,257 B2 | * | 5/2009 | Bonne | 73/23.25 |
| 7,701,578 B1 | * | 4/2010 | Herring | 356/417 |
| 2004/0144733 A1 | | 7/2004 | Cooper et al. | 210/748 |
| 2009/0031785 A1 | * | 2/2009 | Kellner et al. | 73/23.39 |

OTHER PUBLICATIONS

G.W. Rice, J.J. Richard, A.P. D'Silva, V.A. Fassel; Atmospheric Pressure Active Nitrogen Afterglow as a Detector for Gas Chromatography; Anal. Chem. 1981, 53, 1519-1522.

(Continued)

*Primary Examiner* — Daniel Larkin
(74) *Attorney, Agent, or Firm* — Kermit D. Lopez; Luis M. Ortiz; Kevin Soules (57) ABSTRACT

A micro discharge device (MDD) capable of low voltage discharges in a variety of carrier gases for detection and/or ionization includes a sample introduction capillary having a first open end connected to a gas system and a second open end connected to a cylinder comprising a high dielectric constant material. A high voltage electrode can be placed in close proximity to the outer diameter of the cylinder and at a close linear distance to the second open end of the sample introduction capillary. A region can be formed inside the cylinder between the second end of the sample introduction capillary and the high voltage electrode wherein discharge can be located. An optical emission collector can be located through the flow manifold to a receiving location near the high voltage electrode within a region from inside the cylinder between the high voltage electrode and the manifold.

11 Claims, 9 Drawing Sheets

OTHER PUBLICATIONS

K. Chiba, K. Yoshida, K. Tanabe, M. Ozaki, H. Haraguchi, J.D. Winefordner, K. Fuwa; Determination of Ultratrace Levels of Fluorine in Water and Urine Samples by a Gas Chromatopraphic/Atmospheric Pressure Helium Microwave Induced Plasma Emission Spectrometric System; Anal. Chem 1982, 54, 761-764.

D.S. Ballantine, Jr., W.H. Zoller; Collection and Determination of Volatile Organic Mercury Compounds inthe Atmosphere by Gas Chromatography with Microwave Plasma Detection; Anal. Chem, 1984, 56, 1288-1293.

A.H. Mohamad, M. Zerezghi, J. A. Caruso; Determination of Polychlorinated Dibenzo-p-dioxins Using Capillary Gas Chromatography with Microwave-Induced Plasma Detection; Anal. Chem. 1986, 58, 468-471.

C. Bradley, J.W. Carnahan; Oxygen-Selective Microwave-Induced Plasma Gas Chromatography Detector for Petroleum-Related Samples; Anal. Chem. 1988, 60, 858-863.

M. Wu, Z. Liu, P.B. Farnsworth, M.L. Lee; Comprehensive Supercritical Fluid Extraction/Gas Chromatographic Analysis of Organic Compounds in Soil Matrices with an Element-Selective Radiofrequency Plasma Detector; Anal. Chem, 1993, 65, 2185-2188.

S. Pedersen-Bjergaard, T. Greibrokk; On-Column Bromine-and Chlorine-Selective Detection for Capillary Gas Chromatography Using a Radio Frequency Plasma; Anal. Chem. 1993, 65; 1998-2002.

A. Zybin, K. Niemax; GC Analysis of Chlorinated Hydrocarbons in Oil and Chlorophenols in Plant Extracts Applying Element-Selective Diode Laser Plasma Detection; Anal. Chem. 1997, 69, 755-757.

C.Brede, S. Pedersen-Bjergaard, E. Lundanes, T. Greibrokk; Microplasma Mass Spectrometric Detection in Capillary Gas Chromatography; Anal. Chem. 1998, 70, 513-518.

N. A. Stevens, M.F. Borgerding; Effect of Column Flow Rate and Sample Injection Mode on Compound-Independent Calibration Using Gas Chromatography with Atomic Emission Detection; Anal. Chem. 1998, 70, 4223-4227.

J.C.T. Eijkel, H. Stoeri, A. Manz; A dc Microplasma on a Chip Employed as an Optical Emission Detector for Gas Chromatography; Anal. Chem. 2000, 72, 2547-2552.

A. M. Zapata, A. Robbat, Jr.; Performance-Enhanced "Tunable" Capillary Microwave-Induced Plasma Mass Spectrometer for Gas Chromatography Detection; Anal. Chem., 2000, 72, 3102-3108.

\* cited by examiner

MICRO DISCHARGE DEVICE CAPABLE OF LOW VOLTAGE DISCHARGES IN A VARIETY OF CARRIER GASES FOR DETECTION AND/OR IONIZATION

CROSS-REFERENCE TO PROVISIONAL PATENT APPLICATION

This patent application claims priority under 35 U.S.C, §119(e) to provisional patent application Ser. No. 60/990,559, entitled "Micro Discharge Device Capable of Low Voltage Discharges in a Variety of Carrier Gases for Detection and/or Ionization" which was filed on Nov. 27, 2007, the entire disclosure of which is hereby incorporated by reference.

GOVERNMENT RIGHTS STATEMENT

This invention was made with the support of the Government of the United States of America under Contract No. FA8650-04-C-2502 awarded by AFRL Wright Lab/Defense Advanced Research Projects Agency (DARPA). The Unites States Government has certain rights in this invention.

TECHNICAL FIELD

Embodiments are generally related to micro discharge devices. Embodiments are also related to gas chromatograph systems. Embodiments are additionally related to microelectromechanical system (MEMS) based micro discharge devices.

BACKGROUND OF THE INVENTION

Gas chromatography is an analytical technique which entails the separation and often identification of individual compounds, or groups of compounds, within a mixture. A gas chromatograph (GC) takes a small sample of liquid or gas that is introduced into a carrier stream of the same of another gas and identifies the amounts of various compounds within the sample, often in the form of a chromatograph. A chromatograph is a line chart with the horizontal axis identifying different compounds and the vertical axis providing an intensity related to the concentration. The carrier stream typically comprises helium, hydrogen, or nitrogen. The total amount of a compound in a given sample is generally related to the area under the peak associated with that particular compound. A highly sensitive detector can be utilized for the detection of these various compounds passing through a column of the GC. The commonly utilized detectors include, for example, flame ionization detector (FID), nitrogen-phosphorous detector (NPD), electron capture detector, and mass spectrometer. Such conventional detectors, however, are cumbersome or expensive to use, others generate electrons and ions by means of radioactive elements which can be hazardous and not suitable for general applications.

Micro discharge device (MDD) detector can be utilized for detecting the presence of molecules in a gas sample on the basis of their optical emission spectrum as excited and emitted by that discharge. The majority of prior art MDD detectors are designed with a minimum discharge region, which possess a minimal overlap with the analyte's flow path. The problem associated with such detectors is an unacceptable large dead-volume before emission region which makes the device less useful for high efficiency chromatography. Also, many devices have no barrier between the discharge and the electrodes making the devices less durable. Also, such detectors possess moderate to low intensity emissions in helium or other inert noble carrier gases and little to no emissions in an air carrier gas at low voltages.

Figure 1:
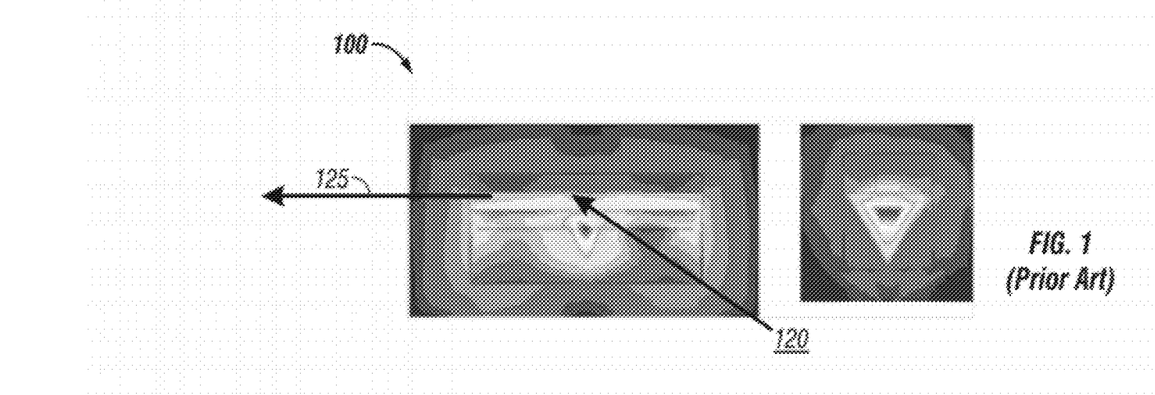
FIG. 1 illustrates an electric field distribution of prior art micro discharge device.

FIG. 1 illustrates an electric field distribution of a prior art micro discharge device 100. The gas flow direction is indicated by arrow 125. As depicted in FIG. 1, the highest electric field region is not in the flow channel. The electric field ratio of the micro discharge device 100 at the middle of the channel as indicated by arrow 120, is equivalent to 3.8. Hence, the MDD 100 requires very high operating voltage to create high electric field strengths in the flow path. The large fields often cause durability issues. Without the very large field, a lower intensity discharge signal results for MDD 100.

Based on the foregoing, it is believed that a need exists for an improved micro discharge device capable of low voltage discharges in a variety of carrier gases for detection and/or ionization as disclosed in greater detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved MDD for gas detection.

It is another aspect of the present invention to provide for an improved MEMS based MDD.

The aforementioned aspects and other objectives and advantages can now be achieved as described herein. A micro discharge device (MDD) capable of low voltage discharges in a variety of carrier gases for detection and/or ionization is disclosed. The MDD generally includes a sample introduction capillary having two ends and adapted to serve as a ground electrode. The sample introduction capillary has a first open end connected to a gas system and a second open end connected to a cylinder comprising a high dielectric constant material. A high voltage electrode can be placed in close proximity to the outer diameter of the cylinder and at a close linear distance to the second open end of the sample introduction capillary. A region formed inside the cylinder between the second end of the sample introduction capillary and the high voltage electrode is the region in which discharge can be located. An optical emission collector, which can be provided in the form of a fiber optic cable, can be located through the flow manifold to a receiving location near the high voltage electrode within a region from inside the cylinder between the high voltage electrode and the manifold.

The MDD can be molded into a housing in order to make the detector more compatible to MEMS features. The cylinder can be sealed around the sample introduction capillary with an epoxy. The cylinder can extend further with the inner diameter of the flow manifold in order to form a gas tight seal. The diameters of the cylinder, the optical emission collector, and the flow manifold can be such that the optical emission collector is positioned along the center axis of the MDD. This provides a self-aligning feature for the MDD that can maximize the amount of the discharge emission collected. The electrodes can be configured such as to create an electric field maximum within the flow path of the gases.

A single, thin dielectric barrier between the electrodes prevents electrode degradation while minimizing breakdown voltages and allows the carrier gases to be utilized at low voltages. The high dielectric barrier, the sample introduction capillary, and placement of the discharge electrodes contain the discharge to a small volume and reduce the dead volume. The self-aligning optical collector of the MDD increases the percentage of the emission captured. The entire device can be hermetically sealed at joints formed between the cylinder and the sample introduction capillary and flow manifold allowing a sample to be either pushed or pulled through the MDD. The MDD described herein can include a completely sealed and localized discharge region, hence, a sample can be directed to any number of other systems before or after the MDD.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 2:
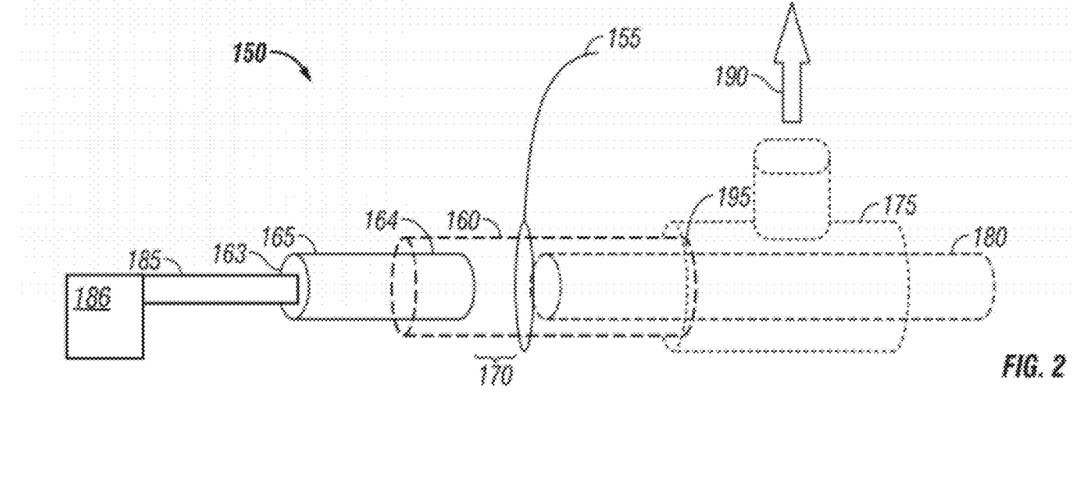
FIG. 2 illustrates a perspective view of a ferrule based MDD, which can be implemented in accordance with a preferred embodiment.

FIG. 2 illustrates a perspective view of a ferrule based micro discharge device (MDD) 150, in accordance with a preferred embodiment. The MDD 150 generally includes a sample introduction capillary 165 having a first open end 163 and a second open end 164. The first open end 163 of the sample introduction capillary 165 can be connected to a gas system 186 such as a gas chromatography column and the second open end 164 can be connected to a cylinder 160. The cylinder 160 comprises a high dielectric constant material that can be configured from a material such as, for example, quartz. The dielectric material 160 can cover approximately 1 cm of the small electrically conductive capillary 165. The inner diameter of the dielectric material 160 can be slightly larger than the outer diameter of the small electrically conductive capillary 165. Furthermore, the dielectric material 160 can extend approximately 1 cm past the end of the capillary 165. These dimensions are described for purposes of clarity and specificity; however, they should not be interpreted in any limiting way. It will be apparent to those skilled in the art that other dimensions can also be utilized without departing from the scope of the invention.

A high voltage electrode 155 can be placed in close proximity to the outer diameter of the cylinder 160 and at a close linear distance to the second open end 164 of the sample introduction capillary 165. A discharge region 170 can be formed inside the cylinder 160 between the second end 164 of the sample introduction capillary 165 and the high voltage electrode 155. The ferrule based MDD 150 further includes an optical emission collector 180 which can be located through a flow manifold 175 to a receiving location near the high voltage electrode 155 within a region from inside the cylinder 160 between the high voltage electrode 155 and the flow manifold 175. The cylinder 160 can extend further out making a gas tight seal 195 with the inner diameter of the flow manifold 175. A gas sample can be passed through a flow inlet 185 of the MDD 150 for detecting the presence of molecules in the gas sample on the basis of their optical emission spectrum as excited and emitted by the MDD 150 and the gas can be emitted through a outlet flow 190, as depicted in FIG. 2.

Figure 3:
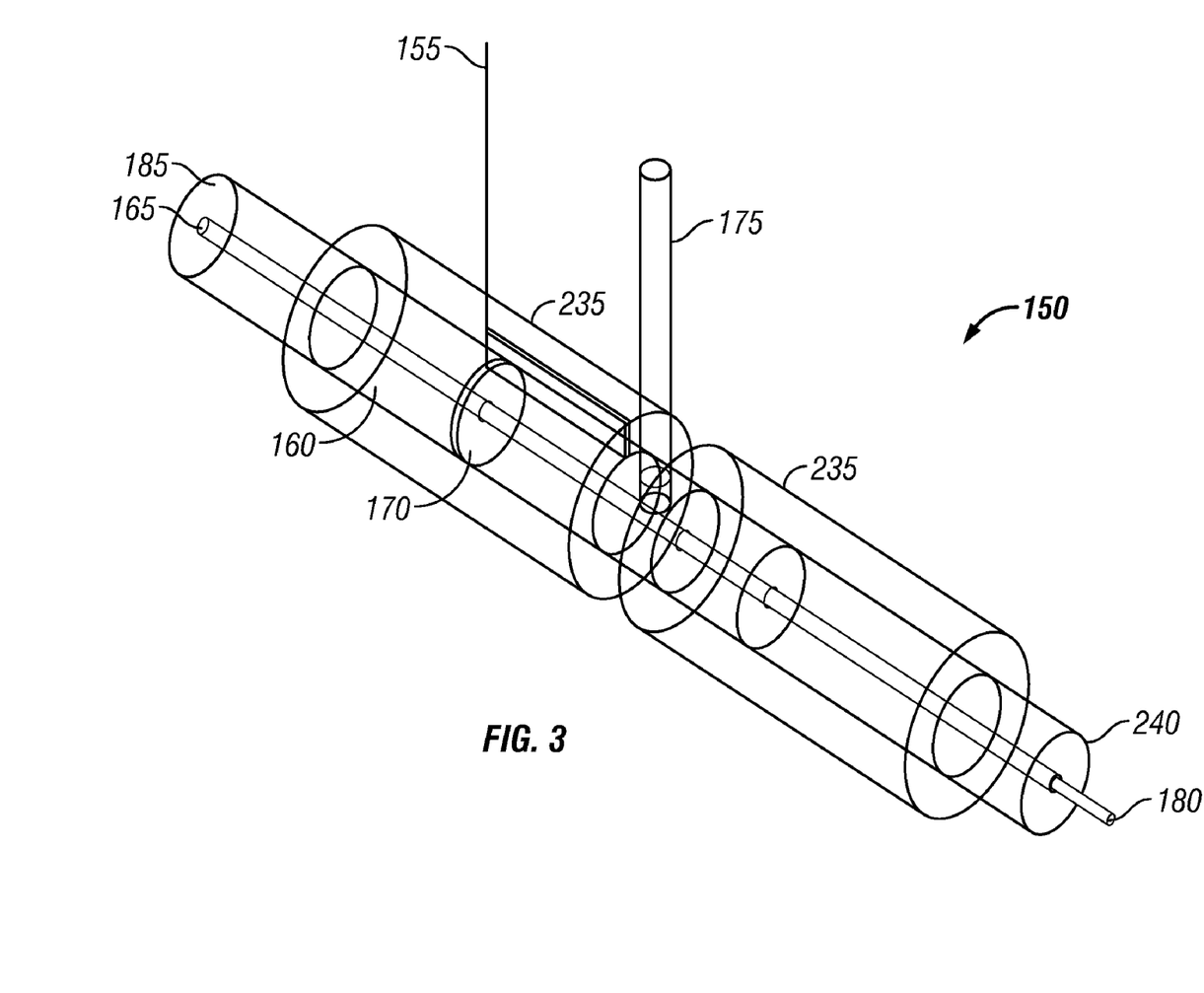
FIG. 3 illustrates a three dimensional view of the ferrule based MDD, which can be implemented in accordance with a preferred embodiment.

FIG. 3 illustrates a three dimensional view of the ferrule based MDD 150, in accordance with a preferred embodiment. Note that in FIGS. 2-9, identical or similar blocks are generally indicated by identical reference numerals. FIG. 3 illustrates an ameliorated view of the MDD 150 illustrated in FIG. 2. The MDD 150 further includes an alignment sleeve 235 and an alignment ferrule 240 for aligning the cylinder 160, the optical emission collector 180 and the flow manifold 175 such that the optical emission collector 180 can be positioned along the center axis of the MDD 150. The alignment ferrule 240 provides a self-aligning feature that can maximize the amount of the discharge emission collected.

The alignment sleeve 235 and the alignment ferrule 240 holds anti-displacement features and anti-flexural features for preventing flexural, rotational or torsional movement of the body portion of the MDD 150. The discharge region 170 can be located over a flow manifold 175, which is formed inside gas tight seal 195 between the end of the electrically conductive capillary 165 and high voltage electrode 155. The sample introduction capillary 165 can also be adapted to serve as a ground electrode. The sample introduction capillary 165 can be sealed around by a non-conductive epoxy. The entire micro discharge device 150 can be hermetically sealed at joints formed between the cylinder 160 and the sample introduction capillary 165 and the flow manifold 175 allowing the sample gas to be either pushed or pulled through the MDD 150.

Figure 4:
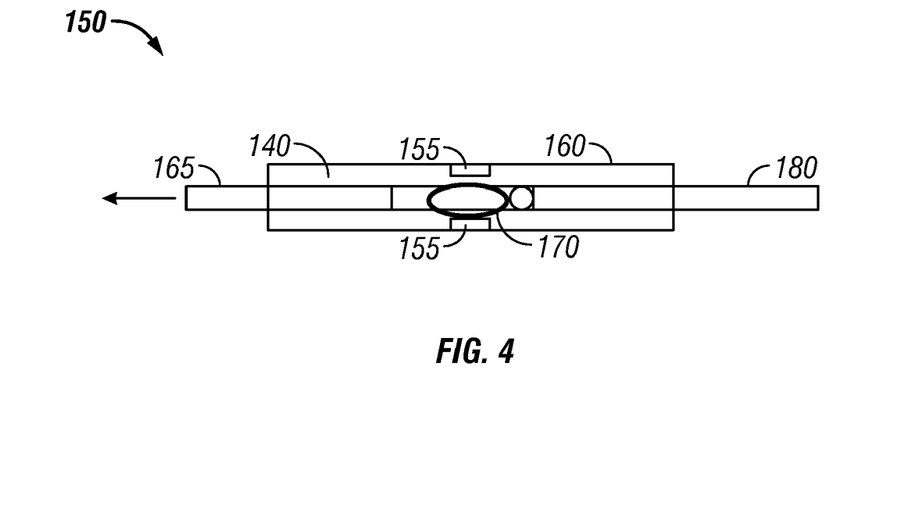
FIG. 4 illustrates a perspective view of a flat MEMS compatible embodiment of the MDD, which can be implemented in accordance with a preferred embodiment.

FIG. 4 illustrates a perspective of a flat MEMS compatible embodiment of the MDD 150, in accordance with a preferred embodiment. The cylinder 160 includes a single, thin dielectric barrier 140 between the two electrodes 155 which prevents electrode degradation while minimizing breakdown voltages and allows all tested carrier gases such as air, nitrogen, and helium to be used at low voltages. The high dielectric barrier 140, sample introduction capillary 165, and placement of the discharge electrodes 155 contain the discharge to a small volume and reduce the dead volume. The electrodes 155 can be configured such as to create an electric field maximum within the flow path of the gases. The self-aligning optical collector 180 is a fiber optic collector, which increases the percentage of the emission captured.

The discharge region 170 formed inside the cylinder 160 between the second end 164 of the sample introduction capillary 165 and the high voltage electrode 155 is the region in which discharge can be located. The flat MEMS compatible MDD creates an electrical discharge within the carrier gas at the discharge region 170 between the electrodes 155. The discharge can be characterized by the creation of plasma. Plasma is electrically conductive due to the relatively high percentage of ions and electrons. During this process, the electrons in the atoms and molecules are excited to higher energy levels. As the electrons return to lower energy levels, photons of light are emitted at different wavelengths which are characteristic of the given atoms or molecules. Accordingly, the discharge has different optical and electrical characteristics depending on whether there are any compounds present other than the carrier gas.

Figure 5:
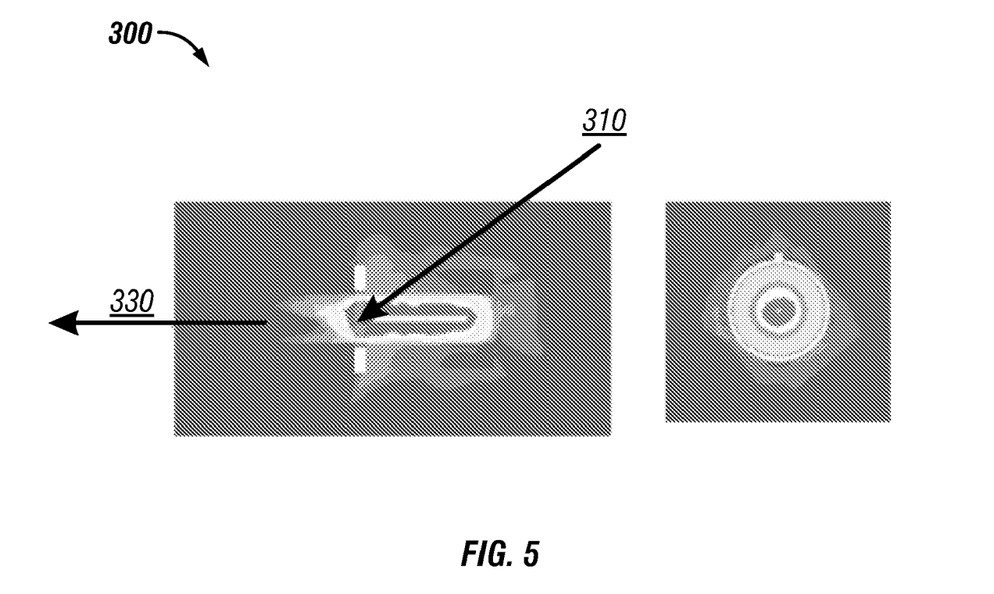
FIG. 5 illustrates an electric field distribution of the ferrule based MDD, which can be implemented in accordance with a preferred embodiment.

FIG. 5 illustrates an electric field distribution 300 of the ferrule based MDD 150, in accordance with a preferred embodiment. The direction of the gas flow is shown by arrow 330. The electric field ratio of the MDD 150 at the middle of the channel, as indicated by arrow 310, is equal to 11.2. The electric field maximum is in the flow channel, which provides a high intensity discharge at very low operating voltage. The electrodes 155 of both the ferrule based MDD 150 and flat MEMS compatible MDD are dielectrically protected such as to provide a high lifespan to the detector.

Figure 6:
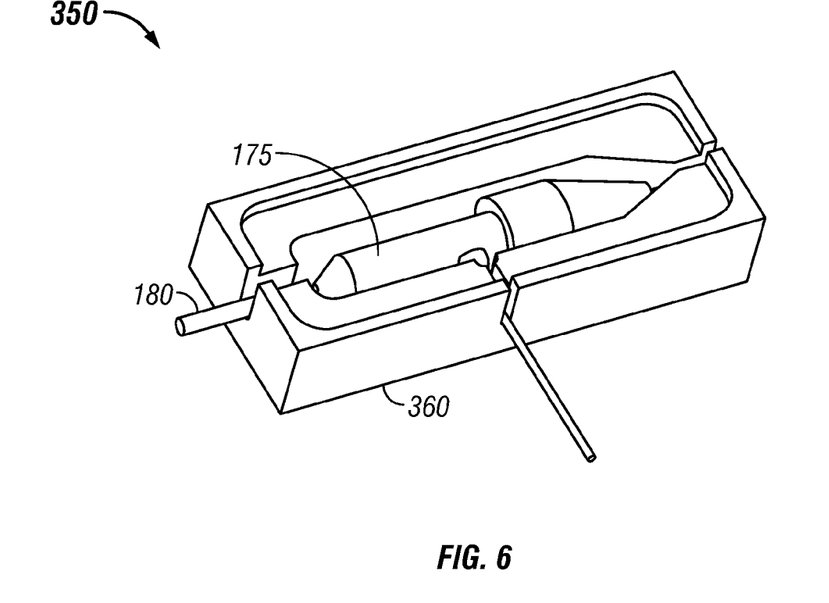
FIG. 6 illustrates a perspective view of a ferrule based MDD associated with a MEMS amenable housing, which can be implemented in accordance with a preferred embodiment.
Figure 7:
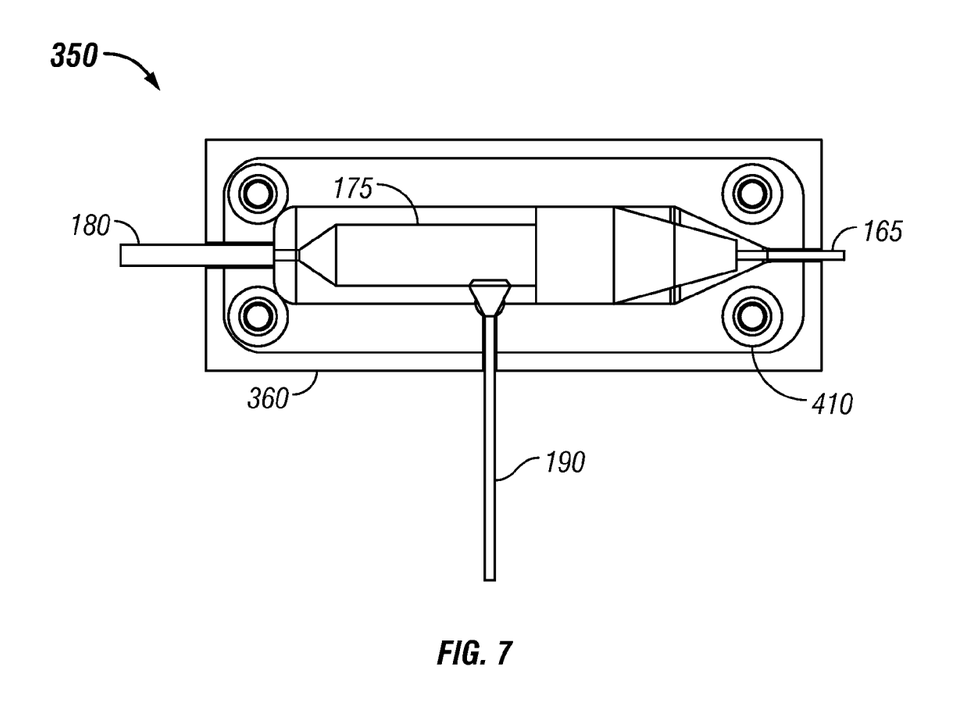
FIG. 7 illustrates a top view of the ferrule based MDD associated with a MEMS amenable housing, which can be implemented in accordance with a preferred embodiment.
Figure 8:
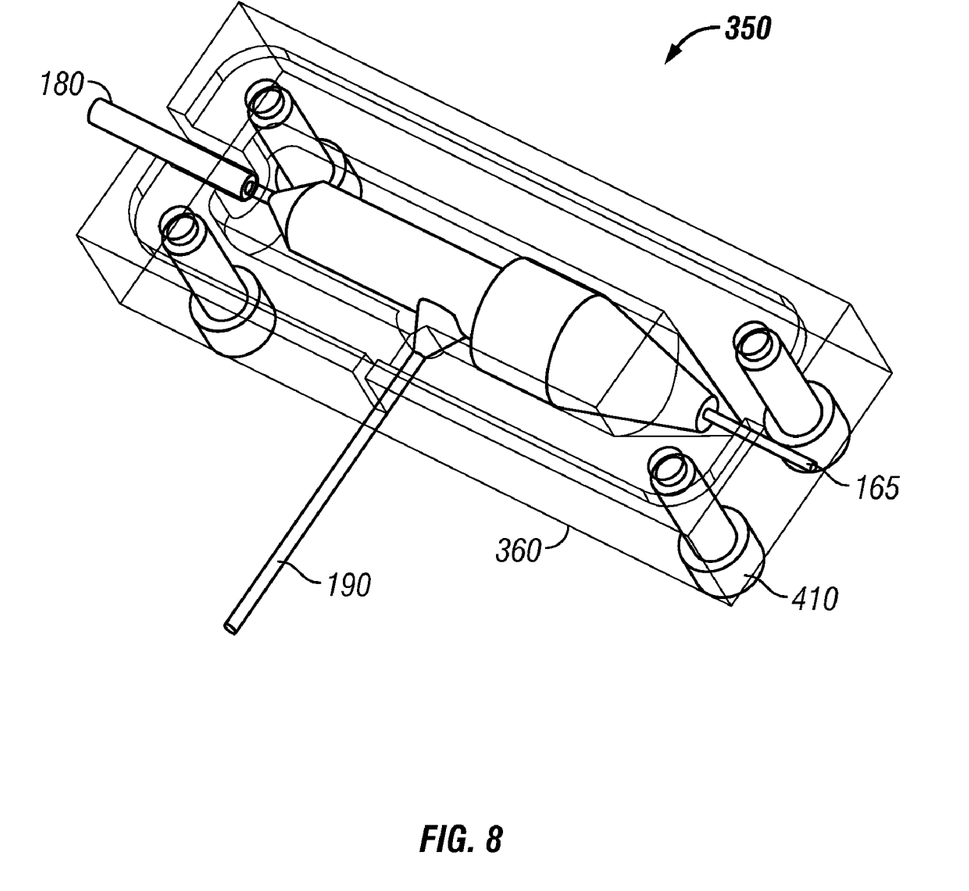
FIG. 8 illustrates a perspective view of the ferrule based MDD associated with a MEMS amenable housing, which can be implemented in accordance with a preferred embodiment.
Figure 9:
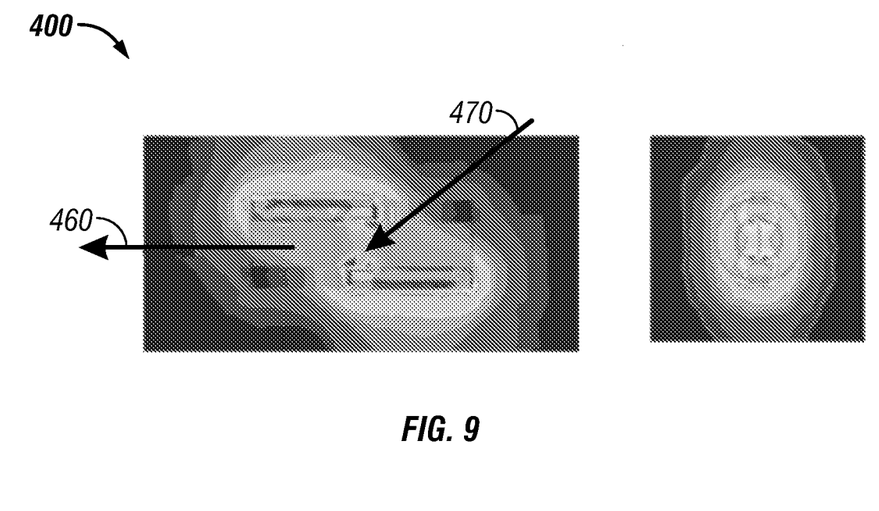
FIG. 9 illustrates an electric field distribution of the flat MEMS compatible embodiment of the MDD, which can be implemented in accordance with a preferred embodiment.

FIG. 6 illustrates a perspective view of a MEMS based MDD 350 associated with a housing 360, in accordance with the preferred embodiment. Again, as reminder, in FIGS. 2-9, identical or similar blocks are generally indicated by identical reference numerals. The MDD 150 can be molded into a housing 360 utilizing connectors 410, as shown in FIG. 7, in order to make the detector 150 more compatible to MEMS features. The self-aligning optical collector 180 of the MEMS-based MDD 350 increases the percentage of the emission captured. The flat MEMS-compatible MDD possesses a very long lifespan and is mass manufacturable. FIGS. 7-9 illustrate designs for a housing 360 to make the ferrule based MDD 150 more MEMS compatible for gas sensor micro-assemblies in accordance with MEMS-based features for carrying out features of the present invention. FIG. 7 illustrates a perspective top view of MEMS based micro discharge detector 350 associated with a housing 360.

FIG. 8 illustrates another view of the MEMS based MDD 350 shown in FIG. 6 for better realization. The electrodes 155 can be configured such as to create an electric field maximum within the flow path of the gases. The flow path of the MEMS-based MDD 350 is such that the ionized sample can be directed into any other system/sensor for further analysis, if desired. The sample gas can be passed through the inlet 163 to the discharge region 170, which flows around the optical emission collector 180 and is directed out of the exhaust port 190 located on the flow manifold 175. The flow path of the MEMS-based MDD 350 is such that the ionized sample can be directed into any other system/sensor for further analysis if desired.

FIG. 9 illustrates an electric field distribution 400 of the MEMS based MDD 350, in accordance with a preferred embodiment. The direction of the gas flow is shown by arrow 460. The electric field ratio of the MEMS based MDD 350 at the middle of the channel, as indicated by arrow 470, is equal to 11.2. The electric field maximum is in the flow channel, which provides a high intensity discharge at low operating voltages.

Figure 10:
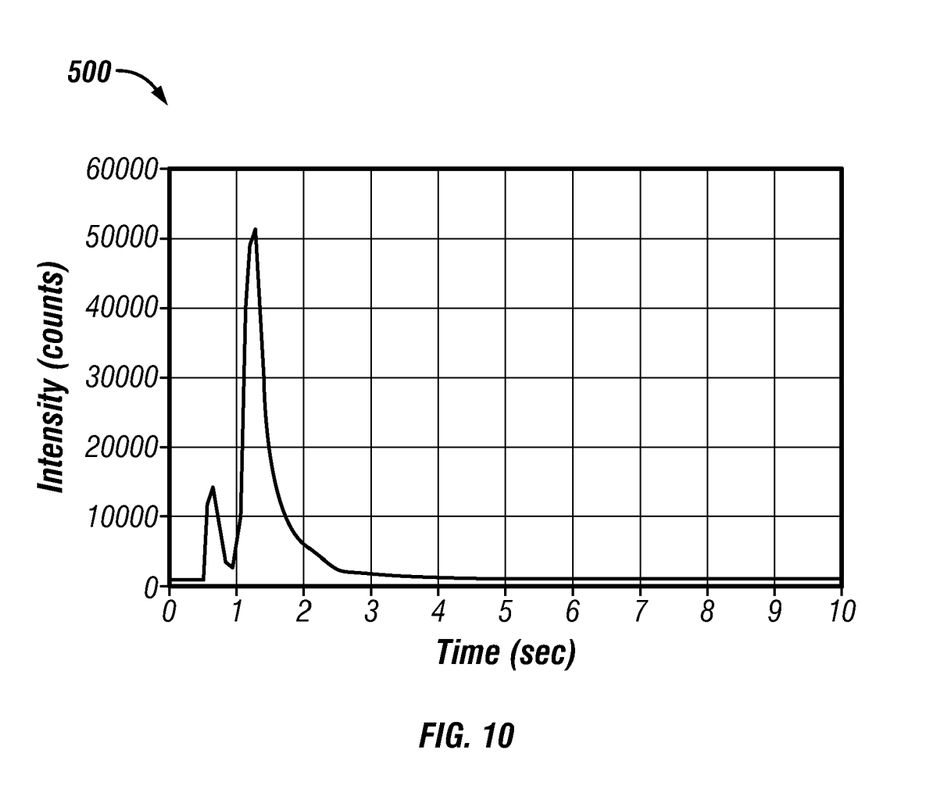
FIG. 10 illustrates a graphical representation illustrating testing of the MDD in helium, which can be implemented in accordance with a preferred embodiment.

FIG. 10 illustrates a graphical representation 500 illustrating testing of the MDD 150 in helium, which can be implemented in accordance with a preferred embodiment. The testing of the MDD 150 include extensive chemical welfare agent detection in air carrier gas and extensive alkane and CWA-simulate detection in helium, nitrogen and air carrier gases. The analysis can be performed either by pushing or pulling the carrier gases in the MDD 150. In particular, the graphical representation 500 depicts the detection of gases C6 and C9 injected into a 20 cm MEMS channel with 5 psi of helium carrier at room temperature.

Figure 11:
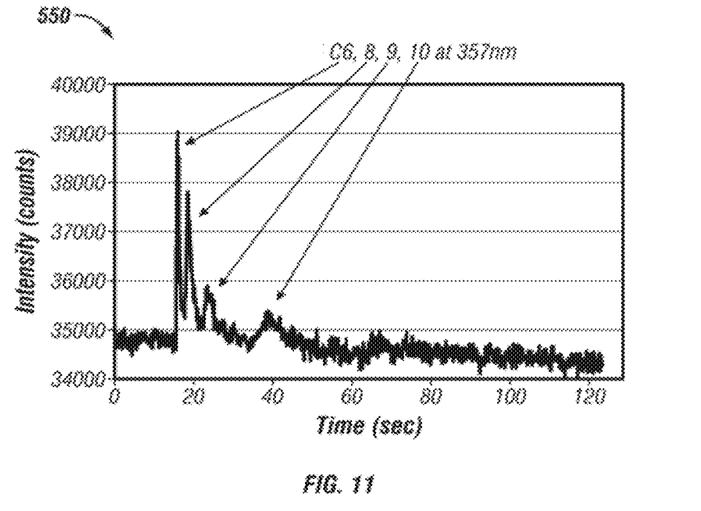
FIG. 11 illustrates a graphical representation illustrating separation of gases with MDD detection, which can be implemented in accordance with a preferred embodiment.

FIG. 11 illustrates a graphical representation 550 illustrating separation of an alkane series within a carrier gas with MDD detection, in accordance with the preferred embodiment. The graphical representation 550 illustrates the separation of gases C6, C8, C9, and C10 with MDD detection at 357 nm, wherein successful separation utilize air as the carrier and discharge gas.

Figure 12:
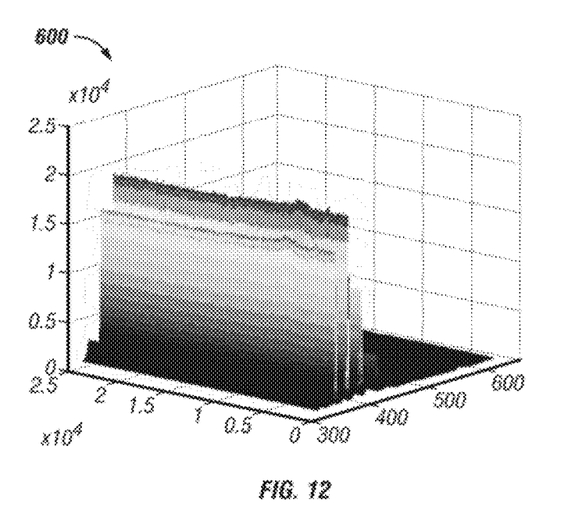
FIGS. 12 and 13 illustrate a three dimensional graphical representation of the MDD data available in detecting a gas chromatogram, which can be implemented in accordance with a preferred embodiment.
Figure 13:
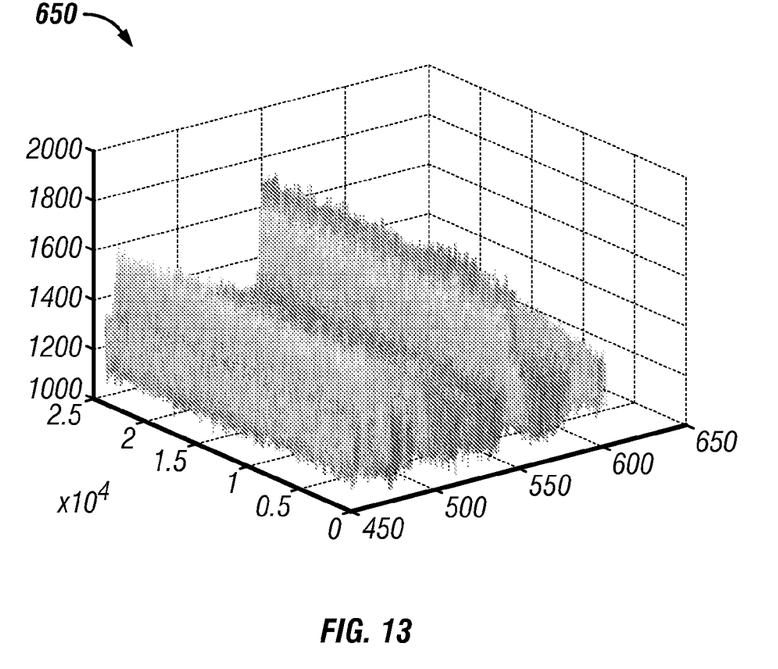

FIGS. 12 and 13 illustrate a three-dimensional graphical representation of the MDD data available in detecting a gas chromatogram, in accordance with the preferred embodiment. The graphical representations 600 and 650 illustrates a three dimensional plot of MDD data set which improves sensitivity by leveraging the data content for signal averaging and chemometrics. The graphical representation 650 illustrates the resulting signal for an air based separation and detection with 30 cm DB-5 column 7 psi head pressure, toluene, DMMP (Dimethyl methylphosphonate), and decane. The third dimension of the data increases the complexity and usefulness and can be utilized to increase sensitivity and specificity.

Figure 14:
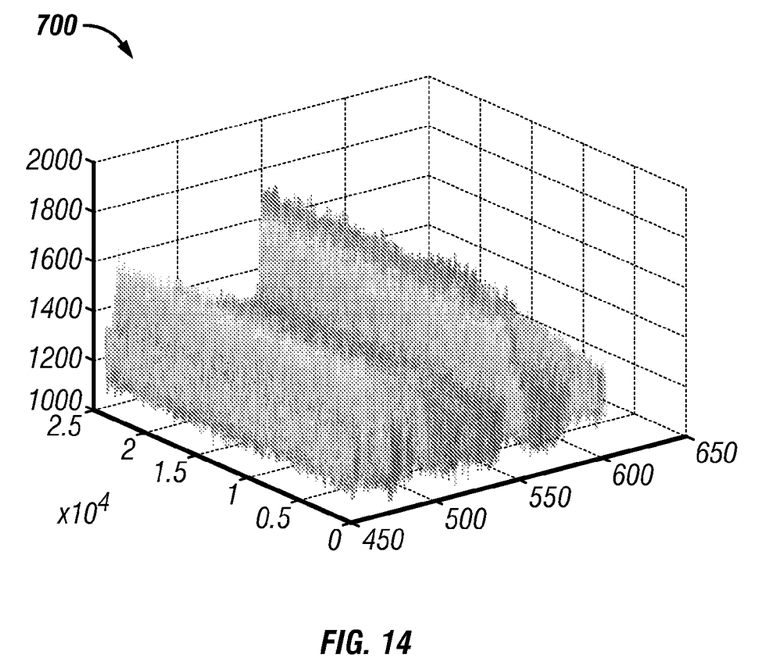
FIGS. 14 and 15 illustrate a graphical representation depicting increase in sensitivity gained by signal averaging to decrease the Gaussian noise level, which can be implemented in accordance with a preferred embodiment.
Figure 15:
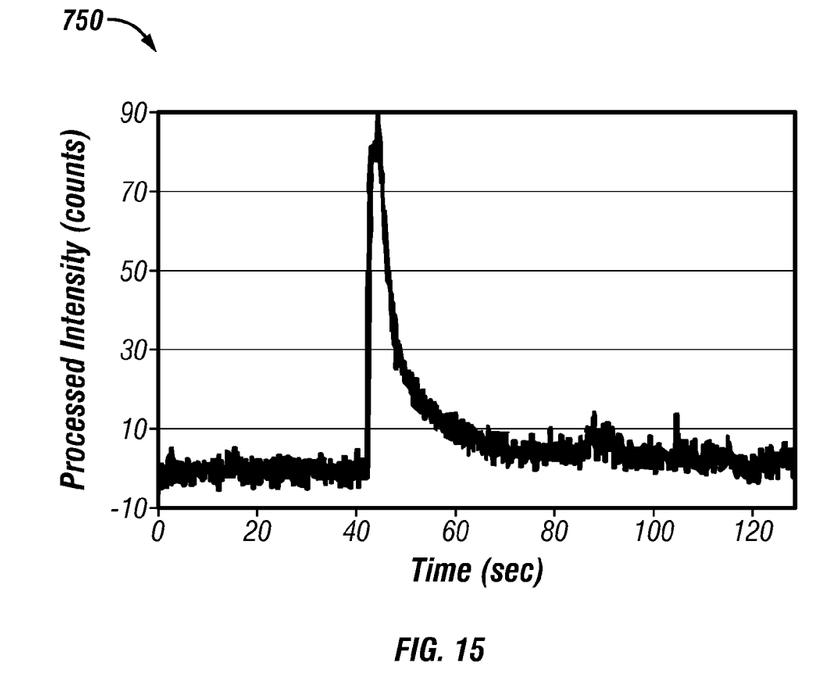

FIGS. 14 and 15 illustrate a graphical representation depicting increase in sensitivity gained by signal averaging to decrease the Gaussian noise level, which can be implemented in accordance with a preferred embodiment The DMMP signal over any one wavelength is weak due to a locally high noise level in the spectra data, which results in a peak that is hard to distinguish from the background in the three-dimensional plot 700. The plot 750 depicts an identical valve injection, under the exact same conditions as the 3-D data as illustrated in FIG. 13 (i.e., 30 cm DB-5, air, 7 psi). The signal comprises an average intensity from 500 nm to 600 nm (a DMMP specific region). The signal averaging of complex 3-D data provides an automatic increased sensitivity.

Figure 16:
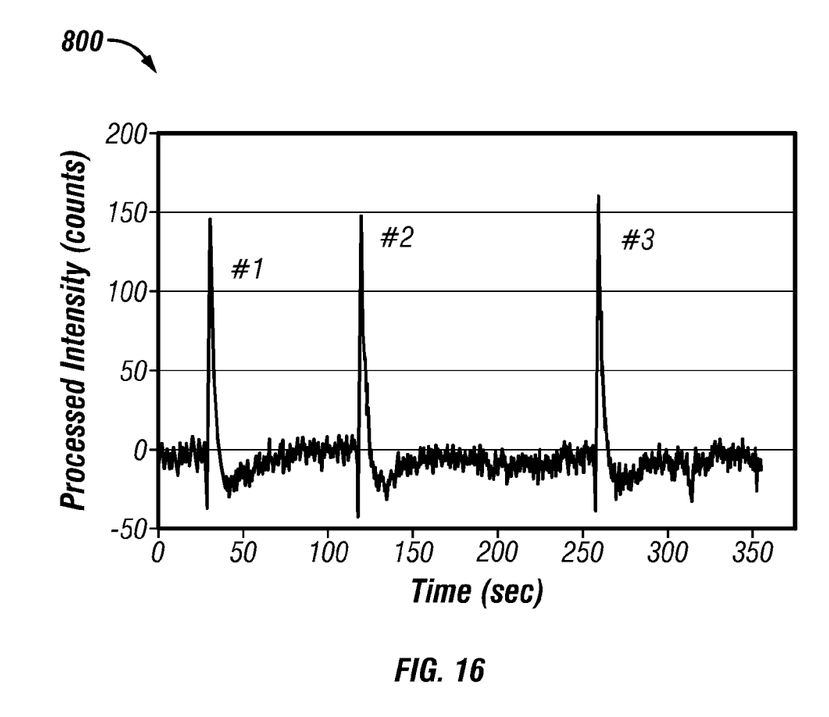
FIG. 16 illustrates a graphical representation illustrating three replicate injections of DMMP through a 30 cm DB-5 column using only background air as the carrier and ionization gas, which can be implemented in accordance with a preferred embodiment.

FIG. 16 illustrates a graphical representation 800 illustrating three replicate injections of DMMP through a 30 cm DB-5 column in air, in accordance with the preferred embodiment. The graphical representation 800 illustrates that toluene does not affect the average emission of DMMP in between range from 500 nm to 600 nm.

The MDD 150 is a multi-channel detector, which provides added analyte selectivity. This selectivity allows analytes that are chromatographically overlapped to be quantitatively resolved via a variety of mathematical procedures generally referred to as chemometrics. The MDD 150 produces low energy plasma in the fluidic path at the end of a phased chromatograph. The fiber optic emission collector 180 directs the optical emission from the compounds passing through the plasma discharge to a spectrometer (not shown), which collects a full emission spectrum.

The analyte and carrier gas molecules that are alike can be detected in the plasma region. Therefore, even when analyte is being detected, its concentration and, therefore, signal is dwarfed by that of the carrier gas. The large concentration difference causes the analyte signal to initially appear very similar to that of the background air. The average of the generic emission can be plotted as the function of time in order to produce traditional 1-D chromatograms.

The MDD 150 described herein can include a completely sealed and localized discharge region 170 hence a sample can be directed to any number of other systems before or after the MDD 150. The ferrule based MDD 150 and MEMS-based MDD 350 described herein provides both universal and selective information about the analytes. The universal information is of high signal to noise allowing for routine detection of sub 100 ppb analytes. However, the selective detection capability of ferrule based MDD 150 and MEMS-based MDD 350 provides analyte specific information and increases the overall resolving power of the phased gas chromatograph. The MDD 150 possesses a very long lifespan due to exposed electrode and is mass manufacturable.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A micro discharge device, comprising:
    a sample introduction capillary having a first open end connected to a gas system and a second open end connected to a cylinder comprising a dielectric material wherein said sample introduction capillary is adapted to serve as a ground electrode;
    an electrode placed proximate to an outer diameter of said cylinder and at a linear distance to said second open end of said sample introduction capillary in order to form a discharge region inside said cylinder between said second end of said sample introduction capillary and said electrode; and
    an optical emission collector located through a flow manifold to a receiving location of said electrode within a region from inside said cylinder between said electrode and said manifold; and
    an alignment sleeve and an alignment ferrule in order to position said cylinder, said optical emission collector and said flow manifold along a center axis.

2. The device of claim 1 wherein said cylinder can be sealed around said sample introduction capillary with an epoxy.

3. The device of claim 1 further comprising a gas tight seal associated with an inner diameter of said flow manifold connected to said cylinder.

4. The device of claim 1 wherein said device is hermetically sealed at joints formed between said cylinder, said sample introduction capillary, and said flow manifold allowing a sample gas to be either pushed or pulled through said device.

5. The device of claim 1 further comprising a housing having said sample introduction capillary, said high voltage electrode, and said optical emission collector formed therein wherein said housing is MEMS compatible for gas sensor micro-assemblies.

6. The device of claim 1 further comprising a gas inlet and a gas outlet.

7. The device of claim 1 wherein said optical emission collector comprises an optical fiber.

8. A micro discharge device, comprising:
    a housing including a sample introduction capillary having a first open end connected to a gas system and a second open end connected to a cylinder comprising a dielectric material wherein said sample introduction capillary is adapted to serve as a ground electrode;
    an electrode placed proximate to an outer diameter of said cylinder and at a linear distance to said second open end of said sample introduction capillary in order to form a discharge region inside said cylinder between said second end of said sample introduction capillary and said electrode, wherein said electrode and an optical emission collector are formed therein;
    said optical emission collector in the form of an optical fiber located through a flow manifold to a receiving location of said electrode within a region from inside said cylinder between said electrode and said manifold; and
    an alignment sleeve and an alignment ferrule in order to position said cylinder, said optical emission collector, and said flow manifold along a center axis.

9. The device of claim 8 wherein said cylinder can be sealed around said sample introduction capillary with an epoxy.

10. The device of claim 8 further comprising a gas tight seal associated with an inner diameter of said flow manifold connected to said cylinder and including a gas inlet and a gas outlet.

11. The device of claim 8 wherein said device is hermetically sealed at joints formed between said cylinder, said sample introduction capillary, and said flow manifold allowing a sample gas to be either pushed or pulled through said device.

* * * * *